United States Patent [19]

Colbert

[11] Patent Number: 4,781,179

[45] Date of Patent: Nov. 1, 1988

[54] ATHLETIC LEG BRACE APPARATUS

[76] Inventor: Michael A. Colbert, 10607 School St., Fairfax, Va. 22030

[21] Appl. No.: 82,581

[22] Filed: Aug. 7, 1987

[51] Int. Cl.$^4$ ............................................... A61F 3/00
[52] U.S. Cl. ..................................................... 128/80 C
[58] Field of Search ................. 128/80 F, 80 C, 87 R, 128/80 R, 77, 88

[56] References Cited

U.S. PATENT DOCUMENTS

| | | | |
|---|---|---|---|
| 1,622,211 | 3/1927 | Sheehan | 128/80 C |
| 4,506,661 | 3/1985 | Foster | 128/80 C |
| 4,572,170 | 2/1986 | Cronk et al. | 128/80 C |
| 4,599,748 | 7/1986 | Garcia | 128/80 C |
| 4,681,097 | 7/1987 | Pansiera | 128/80 C |

Primary Examiner—Robert A. Hafer
Assistant Examiner—Michael Brown
Attorney, Agent, or Firm—Richard C. Litman

[57] ABSTRACT

This device relates to an athletic leg brace apparatus consisting of a flexible upper harness strap, a first- and second-lateral suspension rod having two terminal ends, each having holes or orifices spaced along the longitudinal axis thereof; a first- and second-lower lateral suspension rod having two terminal ends and holes or orifices spaced along the longitudinal axis thereof; a first- and second-shaped, contoured knee protection pad, suitable padded material layers internally disposed to first- and second-lower lateral suspension rods, whereby an upper and lower three-piece modular assemblies are formed. Means for securing said upper and lower assemblies to the upper and lower leg whereby the leg is braced and the knee protected.

1 Claim, 2 Drawing Sheets

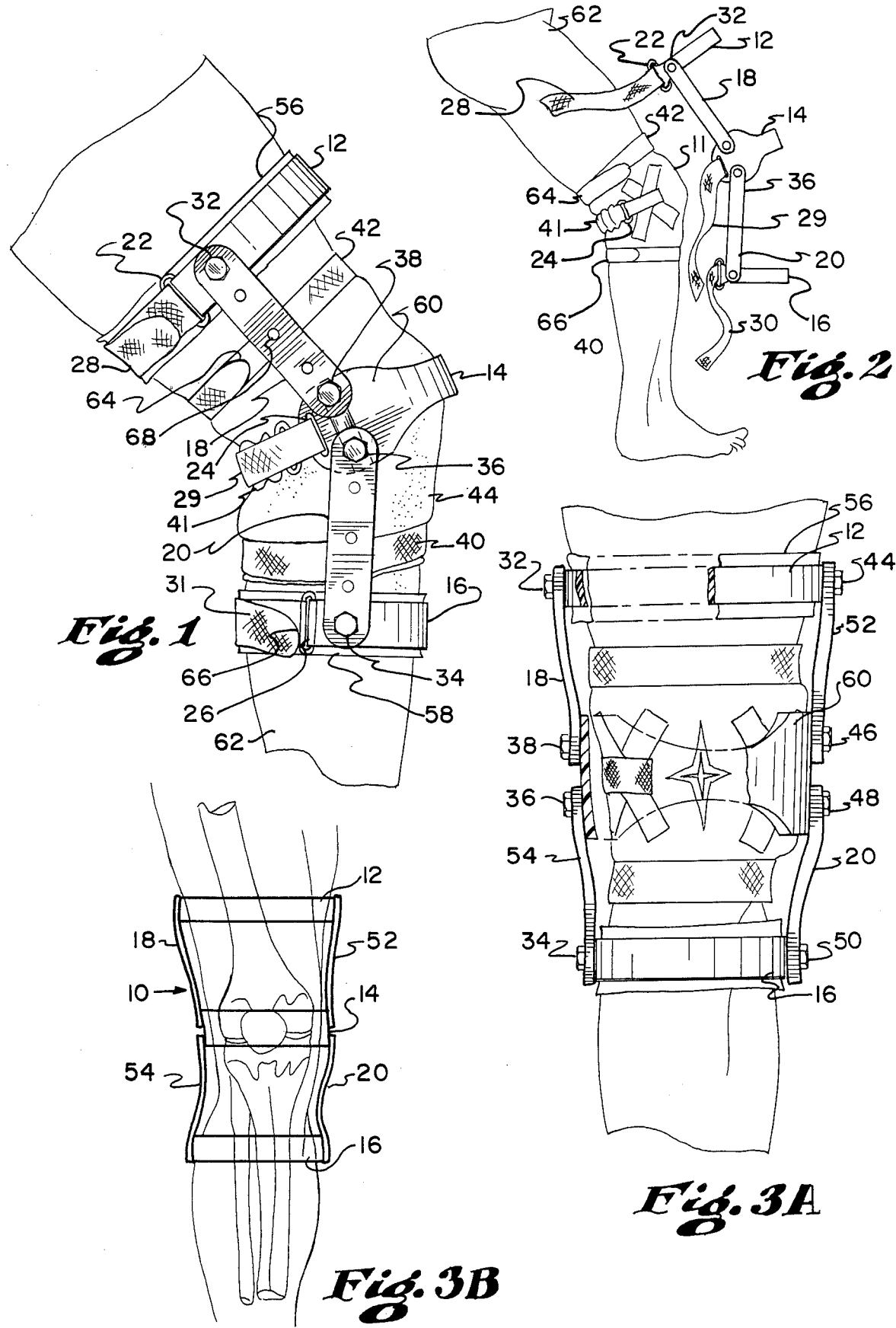

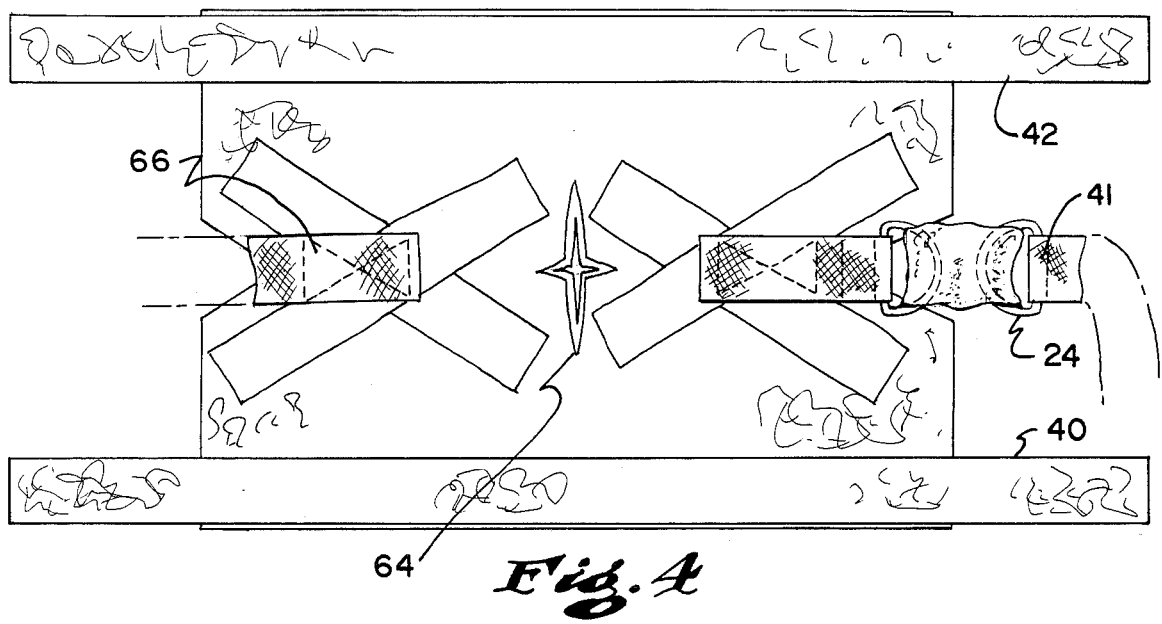
Fig. 4
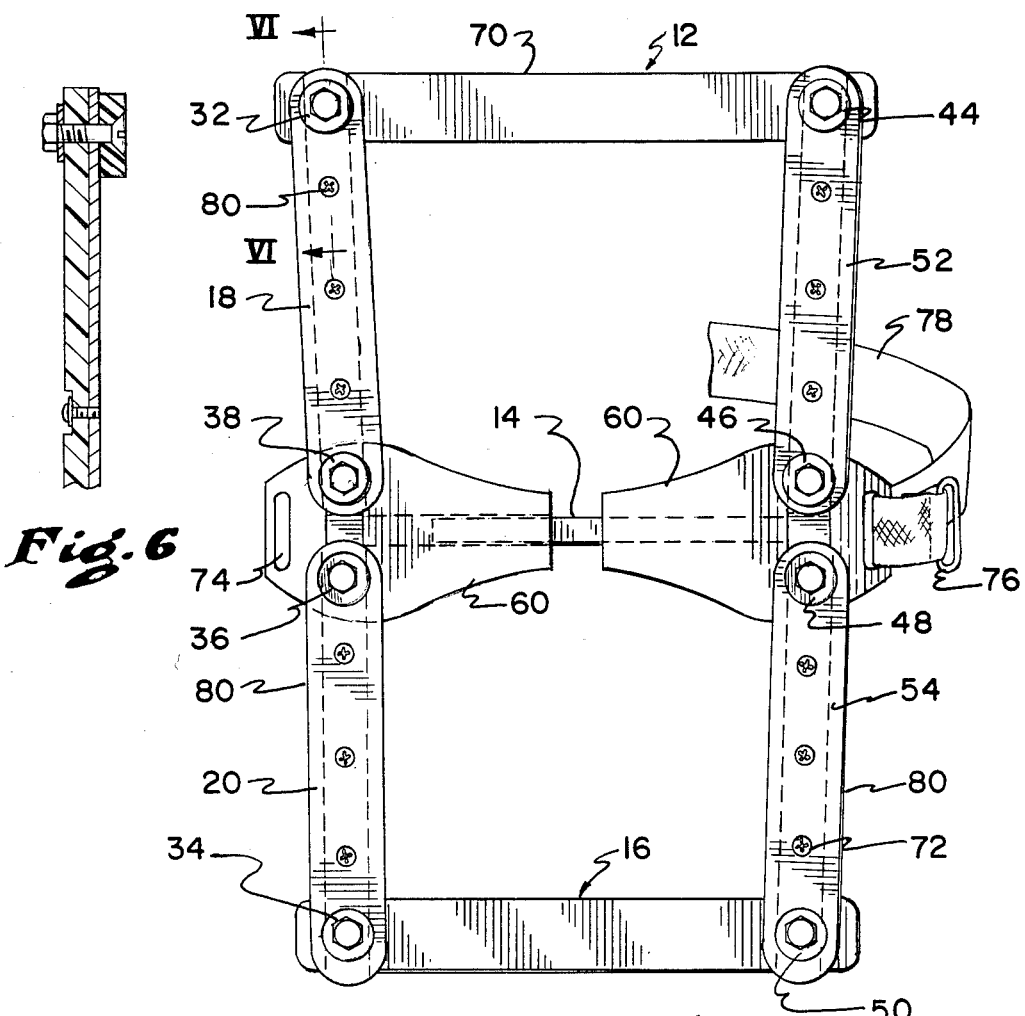
Fig. 6
Fig. 5

ATHLETIC LEG BRACE APPARATUS

FIELD OF INVENTION

This invention relates to athletic leg braces. It specifically relates to an athletic leg brace that flexes with the knee while providing the necessary degree of freedom of movement with a transmittal of lateral forces on the knee to the brace apparatus.

BACKGROUND OF THE INVENTION

In some sporting activities, especially alpine skiing, lateral or shear forces on the knee joint between the upper and lower leg are often in excess of the stress that the knee can withstand. These stresses are not limited to accidents in which bones break, but are often cumulative in their effect, acting to deteriorate the ability of the knee joint to perform its inherent function.

The knee joint with its covering, the patella, is intended to flex substantially in a motion represented by a person rising to a full-standing position, with the back straight, and using only the legs to effect the standing posture. The knee accomplishes this through a physiological system of bone structure, muscles and tendons.

The knee joint pivots about a polycentric center of rotation. Tendons of the upper and lower leg meet at points proximate, above and below, the knee joint. These points of attachment may be considered to be a polycentric center of rotation about which the knee action takes place.

Muscles and tendons, as indicated, do not act upon a single point in the knee joint structure, but rather serve to apply tension along a variety of points which can be represented as constituting a polycentric set of pivot points. This physiological apparatus is, for the most part, dedicated to providing the greatest resiliency and strength in a motion bringing the knee straight up along the front of the torso, with the upper leg hinged to the hip joint.

There is comparatively little musculature or ability of the knee joint to bend or rotate in a direction lateral or sideways to the direction a person is facing. The knee pivots, for the most part, in the direction the feet are facing. Any sideways motion is achieved through the musculature rather than through the action of the knee joint.

For this reason, virtually all athletic brace apparatuses make allowance for the polycentric pivot of the knee, and virtually all strive to reinforce the leg in its most vulnerable position, that is, when excessive lateral forces are applied to the leg. It is the transmittal of these excessive forces away from the vulnerable knee joint that is the objective of the vast majority of these devices, to displace the forces away from the knee. The muscles, tendons and stronger parts of the upper and power leg must absorb the majority of these forces. By transmitting the force to another part of the leg, strain on the knee is thereby relieved.

Forces which are lateral to the normal action of the knee, may be encountered in patients suffering from multiple sclerosis, cerebral palsy, paraplegia, hemiplegia, neuropathies, traumatic lower extremity injuries, and birth defects. This wide variety of diseases and injuries give rise to a condition in which the patient's knee joints have even less resiliency than normal and therefore cannot function to sustain the weight of the individual through the normal action of the knee joint.

In all cases, those arising by certain exercises or those cases arising through a variety of causes indicate above, the individual needs assistance in maintaining balance through an apparatus that can transmit certain forces around the knee joint, thus relieving the knee joint of physical stresses beyond its limit of endurance.

DESCRIPTION OF THE PRIOR ART

Various prior art athletic leg brace devices and the like as well as the apparatuses and method of their construction are known and are found to be examplary of the U.S. prior art. They are:

U.S. Pat. No. 4,450,832 to Waddell discloses a body weight support system for skiing and other activities. A tubular structure is rigid except for a sheathing of flexible material that surrounds and covers the knee joint, allowing it to flex. The brace apparatus, as disclosed, is a unit construction with adjustments only in the straps encircling the leg and only along the lower leg in a vertical direction, that is up and down to lower leg.

U.S. Pat. No. 4,136,404 to Lange teaches a leg brace constructed of a first- and second-lower leg brace member and a first- and second-upper leg brace member where the leg brace members are connected by a ball joint hinge structure. While the device restricts lateral flexure of a skiers upper- and lower-leg portions and transmits these forces to the ski boots, it does not disclose a brace having modular constructio nor a brace having a construction advocating a polycentric pivot of the brace with the natural action of the knee joint.

U.S. Pat. No. 3,844,279 to Konvalin discloses an adjustable leg brace in which elments interconnect and adjust vertically about the wearer's leg. Adjustments extend from the heel of the wearer's shoe up to the calf of the leg. The various elements being slidably disposed one to another and having fasteners that hold the adjusted elements in place.

While each of the recited references disclose a leg brace for use with athletic boots or in conjunction with disabled persons, none of the prior art teaches a simple, modular brace that may be adapted to the wearer's leg quickly and conveniently. Nor do any of the prior art references teach a method of construction that lends itself to simplified manufacturing, the inventorying of few component parts, or the simplified assembly provided by the present invention.

SUMMARY OF THE PRIOR ART

A principle object of this device is to provide a brace apparatus which reinforces the leg in that lateral forces are transmitted away from the vulnerable knee joint. Thus, it is the object of this device to transmit lateral or possibly injurious forces away from the knee, and to thereby relieve these lateral pressures from the knee joint.

A further object is to provide a brace having adaption to the polycentric nature of the flexing knee and allowing a natural flexure of the knee joint, while providing stiffening of the joint in a lateral direction to the knee.

A further object is to provide a modular structure in the brace apparatus. An economy of parts, largely interchangeable, reduces the number of manufactured pieces. By reducing the number of parts and simplifying the construction one can reduce the cost of the brace tothe enduser.

In addition to potential manufacturing cost savings and consumer savings, the object of simplified construction of the brace apparatus provides a method for standardizing contours of various brace elements, which would act to reduce the time needed to make a successful fitting of a brace to the wearer's leg.

BRIEF DESCRIPTION OF THE DRAWING

FIG. 1 is a profile view of the atheltic brace showing the modular brace apparatus in use.

FIG. 2 is an exploded view of the athletic brace showing the various components of the brace apparatus along with illustrating padded straps as underlying the brace apparatus.

FIG. 3 (a) is a front view illustrating the possible leg-contoured shapes of part of the modular brace apparatus.

FIG. 3 (b) is another front view showing the position of the knee joint within the framework of the brace apparatus.

FIG. 4 is a front view illustating a knee strap harness auxiliary to the brace apparatus.

FIG. 5 is an assembly view showing an upper and lower modular construction to the elements of the brace apparatus.

FIG. 6 is a sectional view along line VI—VI of FIG. 5 illustrating fasteners connecting elements of the brace apparatus.

DESCRIPTION OF THE PREFERRED EMBODIMENT

Referring now to the drawings, there is shown in FIG. 1 and 2 a device 10 that has a flexible upper harness 12 pivotably connected to a upper lateral suspension rod 18 by fastener 32.

The flexible upper-harness may be made of any suitable material such that it provides flexibility and snug fit when adapting to the wearer's leg and also has the necessary firmness to transmit forces from upper, lateral-suspension rod 18 to the rest of the affected area of the leg.

The upper lateral suspension rod 18 has two terminal ends; the end pivotably connects to the flexible upper harness 12 while the lower end of which is pivotably connected to flared strap connector 60.

Strap-connector 60 forms a wide lateral pad at the sides of the knees, and flares at the sides to distribute imposed stresses against the knee structure.

Flared strap connector 60 overlays strap 14 which connects both sides of the symetrically formed strap connector 60 on each side of the knee joint.

Knee protector strap 14 extends around the knee, being secured by knee protector buckle 24. An elastic band material 41 underlays knee protector strap 14 to soften the action of the strap against the back of the leg.

Lower, lateral suspension rod 20 has two terminal ends: the upper end pivotably connects to flared strap connector 60 by fastener 36 while the lower end pivotably connects to flexible lower harness 16.

Flexible lower harness 16 is indentical in construction to flexible upper harness 12 in that it is secured behind the wearer's leg by bringing the terminal end of the strap 66 into lower harness buckle 26 and securing it thereto.

Referring to FIG. 2, the upper- and lower-harness assemblies and their corresponding upper- and lower-suspension rods, together with flared knee protector pad 60, are detachable from the leg by unfastening straps 28, 29 and 30, these straps being the binding strap for the flexible upper harness, the knee protector strap, and the flexible lower harness, respectively.

FIG. 3 (a) is a front view of the apparatus, showing the upper and lower harness connected to respective sides of the flared strap-connector and that the upper harness is connected to an internally-positioned upper suspension rod 52 and to an externally-positioned, upper suspension rod 18.

FIG. 3 (a) shows an internally-positioned, lower-suspension rod 20 that pivotably connects at the upper terminal end to flared strap connector 60 while the lower terminal end pivotably connects to flexible lower harness 16. Likewise, externallypositioned, lower-suspension rod 54 pivotably connects along its upper terminal end to flared strap connector 60 and along its lower terminal end to flexible lower harness 16.

Fasteners 32 and corresponding fasteners 34, 36, and 38 can be any type fastener such as a bolt with threaded nut and washer, suitable for connecting said flexible upper harness with the suspension rod.

FIG. 3 (b) is a front view of the appatatus showing suspension rods 18, 20, 52 and 54 contouring to the leg, with respect to the skeletal parts thereof.

FIG. 4 illustrates a method of attaching the underlying padding materials, such as padding material 56 that serves to buffer the action of the flexible upper harness, flexible lower harness and the knee-protector pad against the skin. This underlying hook and loop type materials is affixed to said suspension rods through holes 80 provided along the longitudinal axis of said suspension rods. Said underlying material affixed therethrough with fasteners 78 which may be threaded, such as screws or by any suitable fastening mechanism.

FIG. 5 shows a symmetry in construction in that flexible upper harness 12 and flexible lower harness 16 each are pivotably connected at one terminal end of said suspension rods to externally-positioned suspension rod and an internally-positioned suspension rod, elements 52 and 54, respectively.

Likewise, each suspension rod 18, 20, 52 or 54 is pivotably connected at the other terminal end to flared strap connector 60.

In this manner, by pivotably connecting the flexible upper harness to its respective interior and exterior or lateral suspension rod at one end and pivotably securing the other terminal ends of said interior or exterior positioned suspension rods to the flared strap-connector at the other terminal end, an upper modular unit is thereby formed.

By pivotably connecting flexible lower harness 16 to its respective exterior or laterally-positioned suspension rod and to its interiorally-positioned suspension rod, at the lower terminal ends of the suspension rods, and by pivotably connecting the upper terminal ends of the laterally-positioned and internally-positioned suspension rods to the flared strap connector, a lower modular unit is thereby formed.

The combination of an upper- and lower-modular harness assembly, acting in concert, thereby provides a leg brace acting to distribute lateral stresses away from the knee to those portions of the upper and lower leg proximate to their respective harness straps.

What is claimed is:

1. An athletic leg brace comprising;
   a flexible upper harness attachable about the leg above the knee;
   said upper harness having a strap and buckle for securing said upper harness to said leg;

a pair of upper lateral suspension rods each having two terminal ends and provided with holes spaced along the longitudinal axis thereof;

a knee protector strap positionable across the front of the knee and joined to a pair of contoured knee protection pads;

means pivotally securing said terminal ends of said upper lateral suspension rods respectively to said flexible upper harness strap and said protection pads;

a layer of padded material disposed internally of said upper lateral suspension rods and said upper harness strap;

a flexible lower harness attachable about the leg below the knee, said lower harness having a strap and buckle for securing said lower harness to said leg;

a pair of lower lateral suspension rods each having two terminal ends and provided with holes spaced along the longitudinal axis thereof;

means pivotally securing said terminal ends of said lower lateral suspension rods respectively to said flexible lower harness strap and protection pads;

said layer of padded material disposed internally of said lower lateral suspension rods and said flexible lower harness strap;

said layer of padded material and suspension rods having hook and loop fasteners to affix said layer and rods, on said rods hook and loop fasteners affixed by fastening means comprising said holes;

means for securing said knee protection pads behind the leg; whereby said knee protector strap and upper and lower flexible harness straps enclose the leg above the knee as said upper suspension rods are maintained positioned above and laterally of the knee while said lower suspension rods are maintained positioned below and laterally of the knee;

said knee protection pad securing means comprising adjustable means maintaining said pads positioned across and laterally of the knee cap;

a band of elastic material separate from and cooperating with said knee protector strap means for softening the action of the securing means against the back of the leg; and said band of elastic material being contiguous with said securing means.

* * * * *